(12) United States Patent
Nilsson

(10) Patent No.: US 6,686,457 B1
(45) Date of Patent: Feb. 3, 2004

(54) MATERIAL

(76) Inventor: Kurt Nilsson, Andjaktsv. 6, 226 53, Lund (SE)

( * ) Notice: Subject to any disclaimer, the term of this patent is extended or adjusted under 35 U.S.C. 154(b) by 376 days.

(21) Appl. No.: 09/722,241

(22) Filed: Nov. 27, 2000

(51) Int. Cl.[7] .......................... C07H 15/00; A61K 38/14
(52) U.S. Cl. ...................... 536/4.1; 536/123.1; 536/53; 536/120; 514/2
(58) Field of Search ............................... 536/4.1, 123.1, 536/53, 120; 514/2

(56) References Cited

U.S. PATENT DOCUMENTS 4,238,473 A * 12/1980 Lemieux et al.
5,962,422 A * 10/1999 Bertozzi et al.

* cited by examiner

Primary Examiner—Samuel Barts
Assistant Examiner—Michael C. Henry
(74) Attorney, Agent, or Firm—Smith, Gambrell & Russell, L.L.P.

(57) ABSTRACT

Material characterized by that the material contains at least one biologically active saccharide which is covalently bound via at least one spacer to a crosslinked matrix.

39 Claims, No Drawings

MATERIAL

CROSS REFERENCE TO RELATED APPLICATIONS

This application is a continuation-in-part of Ser. No. 09/091,486, filed Dec. 23, 1996 (U.S. Pat. No. 6,444,655, issued Sep. 3, 2002).

MATERIAL

A material containing so-called matrix to which saccharide has been bound via a spacer is described below.

The active part of the material consists of either:

1. Blood group A—O(CH$_2$)$_n$PhNH—CO—(CH$_2$)$_m$NH—CH$_2$—CH(OH)—CH$_2$—O-Matrix or:

2. Blood group B—O(CH$_2$)$_n$PhNH—CO—(CH$_2$)$_m$NH—CH$_2$—CH(OH)—CH$_2$—O-Matrix where Matrix denotes e.g. specifically, cross-linked agarose, especially of the type Sepharose® Fast Flow, where —O(CH$_2$)$_n$PhNH—CO—(CH$_2$)$_m$NH—CH$_2$—CH(OH)—CH$_2$— consists of spacer to separate the blood group determinant from the Matrix, where n and m, respectively, is an integer, n is for example one of 0, 1, 2, 3 or 4, and m is for example 1, 2, 3, 4, 5, 6 or 7, and where the linkage between —O— and Matrix is to a carbon atom in the Matrix.

Blood group A—O(CH$_2$)$_n$PhNH—CO—(CH$_2$)$_m$NH— and

Blood group B—O(CH$_2$)$_n$PhNH—CO—(CH$_2$)$_m$NH—, respectively, is below called (the) ligand.

The Matrix has a large number of bound molecules of ligand. Examples of bound amount of ligand is 1, 2, 3, 4. 5, 6, 7, 8, 9, 10, 11, 12, 13, 14, 15, 16, 17, 18, 19, 20 mmole per liter of Matrix, or an amount of mmole ligand which is between two of the given values per liter of Matrix.

Example of product 1 above is:

a. GalNAcα1–3(Fucα1–2)Galβ-O(CH$_2$)$_2$PhNH—CO—(CH$_2$)$_5$NH—CH$_2$—CH(OH)—CH$_2$—O-Matrix Other examples are for example product containing a in the same manner bound, higher oligosaccharide, which contains the A-determinant terminally, for example A-determinant of type 1, 2, 3 or 4. Further examples of product 1 are material where a combination of a. and one or more of mentioned blood group A variants, are bound via the same type of spacer as shown above to Matrix.

Example of product 2 is:

b. Galα1–3(Fucl–2)Galβ-O(CH$_2$)$_2$PhNH—CO—(CH$_2$)$_5$NH—CH$_2$—CH(OH)—CH$_2$—O-Matrix Other examples are for example product containing a in the same manner bound, higher oligosaccharide, which contains the B-determinant terminally, for example B-determinant of type 1, 2, 3 or 4. Further examples of product 2 are material where a combination of b. and one or more of mentioned blood group B variants, are bound via the same type of spacer as above to Matrix.

In a variant of the invention, the product in addition contains the following structure:

(HOCH$_2$)$_3$C—NH—CO—(CH$_2$)$_5$NH—CH$_2$—CH(OH)—CH$_2$—O-Matrix where (HOCH$_2$)$_3$C—NH— is a so called Tris-group.

In the production of the product according to the invention can for example be used commercially available activated matrix, for example so called NHS-activated Sepharose® 4 Fast Flow (NHS— is an abbreviation of N-hydroxysuccinimide; this variant of agarose is relatively strongly cross-linked, commercially available), which is present in the form of practically spherical particles. The particle size is chosen in, for example, the interval 45–165 μm. This activated Matrix can be used for covalent binding of Blood group A—O(CH$_2$)$_n$PhNH$_2$—, and Blood group B—O(CH$_2$)$_n$PhNH$_2$, respectively, at, as non-limiting and typical example, pH 7.5 or 8.0, in buffer, for example 0.1 M sodium phosphate as non-limiting example, for e.g. 1, or 2 hours or for 20 hours, and in the example at room temperature. The material is washed for example on a glass filter or under other conditions, for example sterile conditions, with for example buffer and is subsequently treated with for example Tris-HCl buffer to react any remaining reactive groups.

In the production of the product can, as another example, be used so-called epoxy-activated Sepharose® 4 Fast Flow, to which covalently is bound Blood group A—O(CH$_2$)$_n$PhNH—CO—(CH$_2$)$_m$NH—, or to which is bound covalently Blood group B—O(CH$_2$)$_n$PhNH—CO—(CH$_2$)$_m$NH—, ps where n och m are specified above as are Blood group A and Blood group B, respectively.

The products can be used, for example, for extra-corporal removal of blood group A- and blood group B-antibodies, respectively, e.g. for treatment of blood, or for example, before a transplantation over the so-called blood group barrier. The product can for this purpose be filled in a column housing with in- and outflow for passage of e.g blood plasma or whole blood.

The product allows the combination of high flow rate (for example in the interval 20–60 ml/min), minimal drop in pressure over the column, and a good binding capacity also of molecularly larger antibody types, such as IgM. As a non-limiting example can be mentioned single passage of more than one liter blood group A plasma with a flow rate of ca 40 ml/minute through a column with a product volume of 62 ml, and an average particle size of 90 μm, practically eliminated all antibodies reactive against blood group A. Similar result was obtained with blood group B product. The products were built as above from Sepharose® 4 Fast Flow. Different types of column houses can be used. The product functions well in for example the type of column housing used for the product ImmunoSorba®. The column filled with packed matrix, can for example be constructed to allow autoclaving or for example to allow aseptic filling. One or more columns can be used. The column volume is chosen for the application and can for example be of a size of for example 50 ml up to a size of for example 200 ml.

MATERIAL

A material containing so-called matrix to which saccharide has been bound via a spacer is described below.

The active part of the material according to the invention, contains at least one Saccharide part which has been bound via a spacer to a Matrix according to:

Saccharide-spacer-Matrix.

The Matrix consists in general of a polymer, plastic, or a polysaccharide, and can bind a large number of Saccharide-spacer units.

Saccharide symbolizes saccharide which has a biological or other affinity to another molecule, protein or cell. Saccharide can consist of a glycoprotein, a neoglycoprotein, a glycopeptide or a glycosylated amino acid, a glycolipid, or a part, a fragment or a modified variant thereof, or another biologically active di- or trisaccharide or higher oligosaccharide substance.

A few non-limiting examples of biologically active saccharides, spacer and Matrix which can be used according to the invention, are given below.

The materials active part consists, as a non-limiting example, of for example either:

1. Blood group A—O($CH_2$)$_n$PhNH—CO—($CH_2$)$_m$NH—$CH_2$—CH(OH)—$CH_2$—O-Matrix or:

2. Blood group B—O($CH_2$)$_n$PhNH—CO—($CH_2$)$_m$NH—$CH_2$—CH(OH)—$CH_2$—O-Matrix where Matrix denotes e.g. specifically, cross-linked agarose, specifically of the type Sepharose® Fast Flow, where —O($CH_2$)$_n$PhNH—CO—($CH_2$)$_m$NH—$CH_2$—CH(OH)—$CH_2$— is spacer to separate the blood group determinant A— and B—, respectively, from the Matrix, where n and m, respectively, is an integer, n is for example one of 0, 1, 2, 3 or 4, and m is for example 1, 2, 3, 4, 5, 6 or 7, and where the linkage between —O— and Matrix is to a carbon atom in the Matrix.

Saccharide-spacer, for example Blood group A—O($CH_2$)$_n$PhNH—CO—($CH_2$)$_m$NH— and Blood group B—O($CH_2$)$_n$PhNH—CO—($CH_2$)$_m$NH—, respectively, is below called (the) ligand.

The Matrix has a large number of bound molecules of ligand. Examples of bound amount of ligand is 0.01, 0.1, 1, 2, 3, 4, 5, 6, 7, 8, 9, 10, 11, 12, 13, 14, 15, 16, 17, 18, 19, 20 mmole per liter of Matrix, or an amount of mmole which is between two of the above given values per liter of Matrix. Per liter Matrix means here the volume occupied by the ready-to-use Matrix product.

A combination of two or more different saccharides can be used according to the invention, for example as non-limiting example, a combination of Blood group A—O($CH_2$)$_n$PhNH—CO—($CH_2$)$_m$NH—, and Blood group B—O($CH_2$)$_n$PhNH—CO—($CH_2$)$_m$NH—, where both ligands in this example are bound to Matrix.

Non-limiting example of product 1 above is:

a. GalNAcα1–3(Fucα1–2)Galβ-O($CH_2$)$_2$PhNH—CO—($C_2$)$_5$NH—$CH_2$—CH(OH)—$CH_2$O-Matrix Other examples are for example product containing a in the same manner bound, higher oligosaccharide, which contains the A-determinant terminally, for example A-determinant of type 1, 2, 3 or 4. Further examples of product 1 are material where a combination of a. and one or more of mentioned blood group A variants, are bound via the same type of spacer as shown above to Matrix, or via a different type of spacer.

Non-limiting example of product 2 is:

b. Galα1–3(Fucα1–2)Galβ-O($CH_2$)$_2$PhNH—CO—($CH_2$)$_5$NH—$CH_2$—CH(OH)—$CH_2$—O-Matrix Other examples are for example product containing a in the same manner bound, higher oligosaccharide, which contains the B-determinant terminally, for example B-determinant of type 1, 2, 3 or 4. Further examples of product 2 are material where a combination of b. and one or more of mentioned blood group B variants, are bound via the same type of spacer as above to Matrix, or via a different type of spacer.

Instead of the —O($CH_2$)$_2$PhNH— group in the formulas above, another suitable Spacer or part of Spacer can be used, as for example —O($CH_2$)$_n$NH— (n is an integer, for example 1, 2, 3, 4, 5, 6, or 7), or another aliphatic compound, or another aromatic compound. The blood group A- or B-determinant can also be bound to an oligomeric substance acting as Spacer, or part of Spacer, as for example a peptide, for example a peptide consisting of amide bound glycine and glutamic acid residues, for example Gly-(Glu-Gly)n-Glu, Where n is an integer between for example 1 and 20. The linkage between the peptide and the saccharide can then for example be via the —O($CH_2$)$_2$PhNH— group in the formulas above, or via for example —O($CH_2$)$_n$NH—, where the NH-part is bound to the carboxyl group on the side-chain of the Glu-residues in the peptide via a NH—CO— (amide) linkage. —O in —O($CH_2$)$_2$PhNH— and in —O($CH_2$)$_n$NH—, respectively, is then bound glycosidically to the Saccharide.

The peptide can have been coupled to for example NHS-activated Sepharose® 4FF via the α-amino-group on the peptide, and thereafter can the saccharide be bound via —O($CH_2$)$_2$PhNH—, or for example —O($CH_2$)$_n$NH, to the carboxyl group on the Glu-residues in the peptide. This linkage between saccharide and Glu-residues can be achieved by for example carbodiimide-mediated coupling, or by for example succinimide-mediated coupling. Another example of peptide is as above, but containing at least one Lysine residue, where the ε-amino group in the peptide is used for covalent coupling to for example NHS-activated Sepharose® 4FF, with subsequent coupling to coupled peptide of, for example, Saccharide-O($CH_2$)$_2$PhNH—, or of for example Saccharide-O($CH_2$)$_n$NH—, to the peptide according to above. Other linkages can be used according to the invention.

As another non-limiting example of peptide can be mentioned peptide consisting of amide bound Gly and Lys units, for example Gly-(Lys-Gly)n-Gly, where n is an integer between for example 1 and 20. In this case can for example the peptide be bound to the Saccharide via amino groups on the peptide, a N-glycosidic linkage is formed between the reducing end on the Saccharide and the ε-amino group on the Lysine residue(s), and the Saccharide-peptide can be coupled to the Matrix via for example the terminal COO- group on the peptide and amino groups on the Matrix, (by for example carbodiimide or succinimide coupling). In the same manner as for the Gly-Glu-peptide above can also an aliphatic or aromatic spacer be used to bind the Saccharide to the Lysine residues of the peptide, but in this case is, for example, glycosidically bound groups of the type —O(CH)$_2$PhCOO—, or for example —O($CH_2$)$_n$COO—, used for carbodiimide- or succinimide-mediated coupling between Saccharide and Lysine residues in the peptide.

The coupling to the peptide can also be carried out by first coupling the Saccharide part to the amino acid and thereafter form the peptide linkages.

Further examples of Ligand according to the invention, is to use a protein or a polysaccharide as Spacer, or part of Spacer, between Saccharide and Matrix. Here for example a protein, such as serum albumin, or a polysaccharide, such as dextran, is used. The Saccharide is then coupled first to the protein, or the polysaccharide, which then is coupled to the Matrix. The same type of chemistry as exemplified above can, as non-limiting examples, be used to achieve the linkages between Saccharide, protein, or polysaccharide, and Matrix.

To use a peptide, protein or polysaccharide according to what has exemplified above, can in some cases be an advantage to increase the ability of the Material to bind protein, and thereby increase the efficiency of the product according to the invention.

In a variant of the invention, the product in addition contains the following structure:

(HO$CH_2$)$_3$C—NH—CO—($CH_2$)$_5$NH—$CH_2$—CH(OH)—$CH_2$—O-Matrix ps where (HO$CH_2$)$_3$C—NH— is a so called Tris-group.

In the production of the product according to the invention can for example be used commercially available activated Matrix, for example so called NHS-activated Sepharose® 4 Fast Flow (NHS— is an abbreviation of N-hydroxysuccinimide; this variant of agarose is relatively strongly cross-linked, commercially available), which is present in the form of practically spherical particles. The particle size is chosen in, for example, the interval 45–165 µm. This activated Matrix can be used for covalent binding of for example, Blood group A—O(CH$_2$)$_n$PhNH$_2$—, and Blood group B—O(CH$_2$)$_n$PhNH$_2$, respectively, at, as non-limiting and typical example, pH 7.5 or 8.0, in buffer, for example 0.1 M sodium phosphate as non-limiting example, for e.g. 1, or 2 hours or for 20 hours, and in the example at room temperature. The material is washed for example on a glass filter or under other conditions, for example sterile conditions, with for example buffer and is subsequently treated with for example Tris-HCl buffer to react any remaining reactive groups.

In the production of the product according to the invention can, as another example, be used so-called epoxy-activated Sepharose® 4 Fast Flow, to which is bound covalently, for example Blood group A—O(CH$_2$)$_n$PhNH—CO—(CH$_2$)$_m$NH—, or to which is bound covalently Blood group B—O(CH$_2$)$_n$PhNH—CO—(CH$_2$)$_m$NH—, where n och m are specified above as are Blood group A and Blood group B, respectively.

As has been mentioned above, a combination of ligands can also be bound covalently to the Matrix.

The products can be used, for example, for extra-corporal removal of blood group A- and blood group B-antibodies, respectively, e.g. for treatment of blood, or for example, before a transplantation, for example over the blood group barrier. The product can be used in general for different types of transplantation as a part of the treatment of the recipient before and during, and eventually after the transplantation. This to be able to circumvent the problem of blood group incompatibility between donor and recipient. The product can for this purpose be filled into a column housing with in- and outlet for passage through the column of for example blood plasma, or whole blood, from the patient who shall be transplanted or who is undergoing a transplantation procedure. The use of the product is therefore not restricted to for example, blood group incompatible transplantation, but can also be used, for example, for blood group compatible transplantation, to minimize problems in connection with donor and recipient of the same blood group, but of different blood group subgroups, for example A1, A2 etc.

Other non-limiting examples of Saccharide according to the specific examples 1 and 2 above, are structures where the saccharide part consists of Galα1–3Galα-, Galα1–3Galβ-, Galα1–3Galβ1–4Glcβ-, Galα1–3Galβ1–4GlcNAcβ-, Galα1–3Galβ1–4GlcNAcβ1–eGalβ1–4Glcβ-, or of oligomeric ligands such as for example (Galα1–3Galα-)n-, (Galα1–3Galβ-)n-, (Galα1–3Galβ1–4Glcβ-)n-, (Galα1–3Galβ1–4GlcNAcβ-)n-, (Galα1–3Galβ1–4GlcNAcβ1–3Galβ1–4Glcβ-)n-, or (Galα1–3Galα-spacer)n-, (Galα1–3Galβ-spacer)n-, (Galα1–3Galβ1–4Glcβ-spacer)n-, (Galα1–3Galβ1–4GlcNAcβ-spacer)n-, (Galα1–3Galβ1–4GlcNAcβ1–3Galβ1–4Glcβ-spacer)n-, where n is an integer larger than 1. The spacer can be varied and is chosen by the expert, and does not limit the scope of the invention. Non-limiting examples of spacer have been given above. These structures can be of interest to be used in for example a column, for example before and after xenotransplantation to reduce so called xeno-antibodies from the patient's blood (whole blood column) or plasma.

Other carbohydrate structures active towards other antibodies, for example antibodies against cancer-antigens, for example prostate-, breast-, intestine-, or skin cancer, can be used to form Product according to the invention. This can be of interest for example to isolate antibodies from blood or plasma against said antigen and after elution from the Product, be used for treatment of said cancer diseases, or to produce reagents, or for example, to remove an excess of antibody derivatives from blood or plasma in immunotherapy of cancer. Other carbohydrate structures specific for e.g. toxins, virus and/or bacteria, can also be used to, form Product according to the invention. These Products can be used to, for example, purify or eliminate virus and/or bacteria from e.g. whole blood or plasma or from other materials, for example food products or from water.

A combination of two or more different ligands (Saccharide-spacer) bound to Matrix, can be used in the Product according to the invention. The saccharides can then be different, and/or the spacer can be different.

The product according to the invention, allows for example a combination of high flow rate (for example in the interval 20–60 ml/min), minimal drop in pressure over the column, and a good binding capacity also of molecularly larger antibody types, such as IgM. As a non-limiting example can be mentioned single passage of more than one liter blood group A plasma with a flow rate of about 40 ml/minute through a column with product volume of 62 ml, and an average particle size of 90 µm, repeatedly, practically eliminated all antibodies reactive against blood group B. Similar result was repeatedly obtained with blood group B plasma concerning antibodies towards blood group A. The products were built as above from Sepharose® 4 Fast Flow.

One or more columns can be used. The column volume is chosen for the purpose and can be for example of a size of, for example, 10 ml, 20 ml, 40 ml, 60 ml up to a size of for example 200 ml. The column volume can be for example between the given values. Different types of column houses of different dimensions can be used. The product according to the invention functions as non-limiting example in the type of column housing with the dimensions used for the product ImmunoSorba®, (which has protein A as ligand bound to Matrix), which has an inner volume between the porous membranes of about 62 ml (that is allows filling of 62 ml Material according to the invention).

When using Products according to the invention for treatment of plasma, membranes which have a lower porosity and Matrix particles of a lower size can in general be used as compared to the case when the Product is applied for treatment of whole blood. Thus, for example, in the case of treatment of plasma, membrane with porosity of for example 30 micrometer, or membrane with a porosity in the interval 20 till 40 micrometer, and particle size of Matrix of for example 90 micrometer, or Matrix of for example particle size in the interval 40–200 micrometer, can be used. When using Products according to the invention for treatment of whole blood, membrane with porosity of for example 30 micrometer or 70 micrometer, or membrane with a porosity in the interval 20 to 100 micrometer, can be used, and the particle size of the Matrix can be for example 150 micrometer, or the Matrix particle size can be for example in the interval 100–250 micrometer.

The filling of the Product according to the invention in the column can be done with different principal methods. According to the invention, the Product can for example either be autoclaved first and thereafter filled aseptically in the column, or the Product can first be filled in the column and thereafter is the column, which has been filled with Product, autoclaved.

The expert chooses the conditions for the autoclaving and this does not limit the extension of the invention. Non-limiting example of autoclaving is treatment in an autoclave of for example counter-pressure type, which involves treatment under at least 20 minutes at 120° C. or higher and with for example water steam.

The column completely, or partially, filled with Material according to the invention, can for example be constructed to allow autoclaving and/or for example to allow aseptic packing of Material according to the invention. Non-limiting example of autoclavable column is a column with two locks, both equipped with for example identical threads which arc screwed, with help of the threads, outside and at both endings of a cylinder(house), which is equipped with matching threads at the two endings of the cylinder(house). Between each lock and cylinder is before screwing together locks and cylinder, placed a porous membrane (that is two membranes and rings for each column), which allows for passage of plasma or whole blood but not for passage of the Material according to invention. Each membrane is mounted between the lock and the cylinder with for example a silicon ring with a fitting grove of about the same or the same diameter as the cylinder. Every silicon ring has for example a grove which allows for fitting the circular membrane in the grove in the silicon ring. The membrane is mounted in the silicon ring and is placed between the lock and the ending of the cylinder, after which the lock is screwed on the cylinder as described above. The silicon ring with the membrane is therewith enclosed between the lock and the cylinder ending. The same procedure is carried out for the other ending of the cylinder. Each lock has a centrally placed hole with an elevation which allows for connecting a bio-compatible and autoclavable set of tubings equipped with connections of e.g. the Luer type.

Instead of connecting the locks and the cylinder with threads, can be used for example a clip mechanism, where for example the locks are equipped with one or more clips (for example in each one of the locks there are 2, 3, 4, 5, 6, 7, 8, 9, 10, 11, 12, 13, 14, or more separate clips), and the cylinder has on its outer side one or more protruding edge(s) placed below the upper part and above the lower end of the cylinder. The clips can be protruding down from the locks and can for example be equipped with a cavity to allow for a larger flexibility. In this manner the silicon ring and membrane according to the above can be placed between the lock and the respective cylinder ending, and the lock is thereafter pressed on the cylinder, whereupon the clips are pressed under the protruding edges on the cylinder and stays there, and the silicon ring with the porous membrane is consequently sealed tightly between the lock and the cylinder.

In order to fill the so mounted column houses with Material according to the invention, the cylinder part is equipped with a circular opening with a protruding part, which has threads, on the outer side of the cylinder to allow connection of a tubing used for filling of the Material, into the cylinder. After filling of the material in the column housing, a bio-compatible plug with threads which matches the threads of the protruding part on the cylinder. In the center of the plug is a protruding tap which fits into the circular hole of the cylinder and which has a length which corresponds to the height of the protruding part. In this manner an (almost) flat surface is achieved inside the cylinder at the circular opening.

All mentioned components of the column house in the example with autoclavable column house, are autoclavable and biocompatible. Lock, membrane, cylinder, plug, and tubing with luer coupling can be made of biocompatible plastic material.

Column house completely or partially filled with Material according to the invention and equipped with above mentioned closed tubing set and plug can be autoclaved. This facilitates according to the invention the achievement of sterility of the products according to the invention. With earlier methods sterile (aseptic) production and filling conditions have been attempted, which are difficult to achieve.

MATERIAL 2

A material containing so-called matrix to which saccharide has been bound via a spacer is described below.

The active part of the material according to the invention, contains one Saccharide part which has been bound via a spacer to a Matrix according to:

Saccharide-spacer-Matrix.

The Matrix consists in general of a polymer, plastic, or a polysaccharide, and can bind a large number of Saccharide-spacer units.

Saccharide symbolizes saccharide which has a biological or other affinity to another molecule, protein or cell. Saccharide can consist of a glycoprotein, a glycopeptide or a glycosylated amino acid, a glycolipid, or a part, a fragment or a modified variant thereof, or another biologically active di- or trisaccharide or higher oligosaccharide substance.

A few non-limiting examples of biologically active saccharides, spacer and Matrix which can be used according to the invention, are given below.

The materials active part consists of for example either:

1. Blood group A—O($CH_2$)$_n$PhNH—CO—($CH_2$)$_m$NH—$CH_2$—CH(OH)—$CH_2$—O-Matrix or:

2. Blood group B—O($CH_2$)$_n$PhNH—CO—($CH_2$)$_m$NH—$CH_2$—CH(OH)—$CH_2$—O-Matrix where Matrix denotes e.g. specifically, cross-linked agarose, specifically of the type Sepharose® Fast Flow, where —O($CH_2$)$_n$PhNH—CO—($CH_2$)$_m$NH—$CH_2$—CH(OH)—$CH_2$— is spacer to separate the blood group determinant A— and B—, respectively, from the Matrix, where n and m, respectively, is an integer, n is for example one of 0, 1, 2, 3 or 4, and m is for example 1, 2, 3, 4, 5, 6 or 7, and where the linkage between —O— and Matrix is to a carbon atom in the Matrix.

Blood group A—O($CH_2$)$_n$PhNH—CO—($CH_2$)$_m$NH— and

Blood group B—O($CH_2$)$_n$PhNH—CO—($CH_2$)$_m$NH—, respectively, is below called (the) ligand.

The Matrix has a large number of bound molecules of ligand. Examples of bound amount of ligand is 1, 2, 3, 4, 5, 6, 7, 8, 9, 10, 11, 12, 13, 14, 15, 16, 17, 18, 19, 20 mmole per liter of Matrix, or an amount of mmole which is between two of the above given values per liter of Matrix.

Example of product 1 above is:

a. GalNAcα1–3(Fucα1–2)Galβ-O($CH_2$)$_2$PhNH—CO—($CH_2$)$_5$NH—$CH_2$—CH(OH)—$CH_2$—O-Matrix Other examples are for example product containing a in the same manner bound, higher oligosaccharide, which contains the A-determinant terminally, for example A-determinant of type 1, 2, 3 or 4. Further examples of product 1 are material where a combination of a. and one or more of mentioned blood group A variants, are bound via the same type of spacer as shown above to Matrix.

Example of product 2 is:

b. Galα1–3(Fucα1–2)Galβ-O($CH_2$)$_2$PhNH—CO—($CH_2$)$_5$NH—$CH_2$—CH(OH)—$CH_2$—O-Matrix.

Other examples are for example product containing a in the same manner bound, higher oligosaccharide, which contains the B-determinant terminally, for example B-determinant of type 1, 2, 3 or 4. Further examples of product 2 are material where a combination of b. and one or more of mentioned blood group B variants, are bound via the same type of spacer as above to Matrix.

In a variant of the invention, the product in addition contains the following structure:

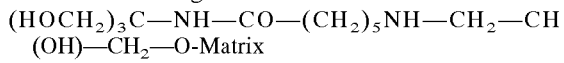

where $(HOCH_2)_3C—NH—$ is a so called Tris-group.

In the production of the product according to the invention can for example be used commercially available activated Matrix, for example so called NHS-activated Sepharose® 4 Fast Flow (NHS— is an abbreviation of N-hydroxysuccinimide; this variant of agarose is relatively strongly cross-linked, commercially available), which is present in the form of practically spherical particles. The particle size is chosen in, for example, the interval 45–165 $\mu$m. This activated Matrix can be used for covalent binding of Blood group $A—O(CH_2)_nPhNH_2—$, and Blood group $B—O(CH_2)_nPhNH_2$, respectively, at, as non-limiting and typical example, pH 7.5 or 8.0, in buffer, for example 0.1 M sodium phosphate as non-limiting example, for e.g. 1, or 2 hours or for 20 hours, and in the example at room temperature. The material is washed for example on a glass filter or under other sterile conditions, with for example buffer and is treated with for example Tris-HCl buffer to react any remaining reactive groups.

In the production of the product according to the invention can, as another example, be used so-called epoxy-activated Sepharose® 4 Fast Flow, to which is covalently bound Blood group $A—O(CH_2)_nPhNH—CO—(CH_2)_mNH—$,
or to which is covalently bound Blood group $B—O(CH_2)_nPhNH—CO—(CH_2)_mNH—$,
where n och m are specified above as are Blood group A and Blood group B, respectively.

The products can be used, for example, for extra-corporal removal of blood group A- and blood group B-antibodies, respectively, e.g. for treatment of blood, or for example, before a transplantation, for example over the blood group barrier. The product can for this purpose be filled into a column housing with in- and outlet for passage through the column of for example blood plasma or whole blood Other non-limiting examples of Saccharide according to the specific examples 1 and 2 above, are structures where the saccharide part consists of Galα1–3Galα-, Galα1–3Galβ-, Galα1–3Galβ1–4Glcβ-, Galα1–3Galβ1–4GlcNAcβ-, Galα1–3Galβ1–4GlcNAcβ1–3Galβ1–4Glcβ-, or of oligomeric ligands, such as for example (Galα1–3Galα-)n-, (Galα1–3Galβ-)n-, (Galα1–3Galβ1–4Glcβ-)n-, (Galα1–3Galβ1–4GlcNAcβ-)n-, (Galα1–3Galβ1–4GlcNAcβ1–3Galβ1–4Glcβ-)n-, or (Galα1–3Galα-spacer)n-, (Galα1–3Galβ-spacer)n-, (Galα1–3Galβ1–4Glcβ-spacer)n-, (Galα1–3Galβ1–4GlcNAcβ-spacer)n-, (Galα1–3Galβ1–4GlcNAcβ1–3Galβ1–4Glcβ-spacer)n-, where n is an integer larger than 1. The spacer can be varied and is chosen by the expert, and does not limit the scope of the invention.

The product allows a combination of high flow rate (for example in the interval 20–60 ml/min), minimal drop in pressure over the column, and a good binding capacity also of molecularly larger antibody types, such as IgM. As a non-limiting example can be mentioned single passage of more than one liter blood group A plasma with a flow rate of about 40 ml/minute through a column with product volume of 62 ml, and an average particle size of 90 $\mu$m, repeatedly, practically eliminated all antibodies reactive against blood group B. Similar result was repeatedly obtained with blood group B plasma concerning antibodies towards blood group A. The products were built as above from Sepharose® 4 Fast Flow.

One or more columns can be used. The column volume is chosen for the purpose and can be for example of a size of for example, 60 ml up to a size of for example 200 ml. Different types of column houses of different dimensions can be used. The product according to the invention functions as non-limiting example in the type of column housing with the dimensions used for the product ImmunoSorba®, (which has protein A as ligand bound to Matrix), which has an inner volume between the porous membranes of about 62 ml (that is allows filling of 62 ml Material according to the invention).

When using Products according to the invention for treatment of plasma, membranes which have a lower porosity and Matrix particles of a lower size can in general be used as compared to the case when the Product is applied for treatment of whole blood. Thus, for example, in the case of treatment of plasma, membrane with porosity of for example 30 micrometer, or membrane with a porosity in the interval 20 till 40 micrometer, and particle size of Matrix of for example 90 micrometer, or Matrix of for example particle size in the interval 40–200 micrometer, can be used. When using Products according to the invention for treatment of whole blood, membrane with porosity of for example 30 micrometer or 70 micrometer, or membrane with a porosity in the interval 20 to 100 micrometer, can be used, and the particle size of the Matrix can be for example 150 micrometer, or the Matrix particle size can be in the interval 100–250 micrometer.

The column, completely or partially filled with Material according to the invention, can for example be constructed to allow autoclaving and/or for example to allow aseptic packing of Material according to the invention. Non-limiting example of autoclavable column is a column with two locks, both equipped with for example identical threads which are screwed, with help of the threads, outside and at both endings of a cylinder(house), which is equipped with matching threads at the two endings of the cylinder(house). Between each lock and cylinder is before screwing together locks and cylinder, placed a porous membrane (that is two membranes and rings for each column), which allows for passage of plasma or whole blood but not for passage of the Material according to invention. Each membrane is mounted between the lock and the cylinder with for example a silicon ring with a fitting grove of about the same or the same diameter as the cylinder. Every silicon ring has for example a grove which allows for fitting the circular membrane in the grove in the silicon ring. The membrane is mounted in the silicon ring and is placed between the lock and the ending of the cylinder, after which the lock is screwed on the cylinder as described above. The silicon ring with the membrane is therewith enclosed between the lock and the cylinder ending. The same procedure is carried out for the other ending of the cylinder. Each lock has a centrally placed hole with an elevation which allows for connecting a bio-compatible and autoclavable set of tubings equipped with connections of e.g. the Luer type.

Instead of connecting the locks and the cylinder with threads, can be used for example a clip mechanism, where the locks are equipped with one or more clips, and the cylinder has on its outer side protruding edges placed below the upper part and above the lower end of the cylinder. In this manner the silicon ring and membrane according to the above can be placed between the lock and the respective cylinder ending, and the lock is thereafter pressed on the cylinder, whereupon the clips are pressed under the protruding edges on the cylinder and stays there, and the silicon ring with the porous membrane is consequently sealed tightly between the lock and the cylinder.

In order to fill the so mounted column houses with Material according to the invention, the cylinder part is equipped with a circular opening with a protruding part, which has threads, on the outer side of the cylinder to allow connection of a tubing used for filling of the Material into the cylinder. After filling of the material in the column housing, a bio-compatible plug with threads which matches the threads of the protruding part on the cylinder. In the center of the plug is a protruding tap which fits into the circular hole of the cylinder and which has a length which corresponds to the height of the protruding part. In this manner an (almost) flat surface is achieved inside the cylinder at the circular opening.

All mentioned components of the column house in the example with autoclavable column house, are autoclavable and bio-compatible. Lock, membrane, cylinder, plug, and tubing with luer coupling can be made of bio-compatible plastic material.

Column house completely or partially filled with Material according to the invention and equipped with above mentioned closed tubing set and plug can be autoclaved. This facilitates according to the invention the achievement of sterility of the products according to the invention. With earlier methods sterile (aseptic) production and filling conditions have been attempted, which are difficult to achieve.

What is claimed is:

1. A material comprising
   a saccharide-spacer-matrix
   where the saccharide denotes a mono-, di- tri- or higher oligosaccharide, which is glycosidically linked to the matrix via the spacer having the formula:

—O($CH_2$)$_n$PhNH—CO—($CH_2$)$_m$NH—$CH_2$—CH(OH)—$CH_2$—O—,

—O($CH_2$)$_n$NH— or —N(Ac)—($CH_2$)$_n$NH—, where Ac is an acetyl group and n and m is an integer 0, 1, 2, 3, 4, 5, 6, or 7,
   or where the spacer contains a mono-, di-, or oligosaccharide, a polysaccharide, a peptide, another oligomeric substance, or a protein.

2. The material according to claim 1 where matrix denotes a plastic or a polysaccharide.

3. The material according to claim 1 which has been autoclaved.

4. The material according to claim 1 where the peptide consists of amide bound glycine and glutamic acid residues.

5. The material according to claim 1 where the peptide consists of Gly-(Glu-Gly)n-Glu, where n is an integer between 1 and 20.

6. The material according to claim 1 where the saccharide-spacer consists of 1, 2, 3, 4, 5, 6, 7, 8, 9, or 10 or more saccharide units bound to each oligomeric spacer.

7. The material according to claim 1 where the peptide contains at least one lysine residue, where ε-amino group in the lysine residue of the peptide is covalently coupled to the matrix.

8. The material according to claim 1 where the peptide consists of amide bound Gly and Lys units.

9. The material according to claim 1 where the peptide consists of Gly-(Lys-Gly)n-Gly, where n is an integer between 1 and 20.

10. The material according to claim 1 where the peptide consists of Ac-Lys-(ε-amino)-Gly-Glu-Gly-Glu-Gly-Glu-Gly-Glu-Gly-Glu-Gly-Glu-Gly-amide.

11. The material according to claim 1 where the peptide is coupled first to activated matrix, with subsequent coupling of saccharide-O($CH_2$)$_n$PhNH$_2$, or of saccharide-O($CH_2$)$_n$NH$_2$, to Glu residues of the peptide and where n is an integer from 1 to 7.

12. The material according to claim 1 where the peptide is bound to saccharide-O($CH_2$)$_n$PhNH$_2$, or to saccharide-O($CH_2$)$_n$NH$_2$, via Glu residues of the peptide, and where n is an integer from 1 to 7, with subsequent coupling of the resulting saccharide-peptide conjugate (saccharide-spacer) to the matrix.

13. The material according to claim 1 where the peptide is coupled to NHS-activated matrix, with subsequent coupling of saccharide-O($CH_2$)$_n$PhNH$_2$, or of saccharide-O($CH_2$)$_n$NH$_2$, to Glu residues of the peptide and where n is an integer from 1 to 7.

14. The material according to claim 1 where the lysine residue of the peptide is coupled to NHS-activated matrix, with subsequent coupling of saccharide-O($CH_2$)$_n$PhNH$_2$, or of saccharide-O($CH_2$)$_n$NH$_2$, to Glu residues of the peptide and where n is an integer from 1 to 7.

15. The material according to claim 1 where coupling of saccharide-O($CH_2$)$_n$PhNH$_2$, or of saccharide-O($CH_2$)$_n$NH$_2$, to Glu residues of the peptide is via a carbodiimide mediated reaction and n is an integer from 0 to 7.

16. The material according to claim 1 where the lysine residue of the peptide is coupled to NHS-activated cross-linked agarose, with subsequent coupling of saccharide-O($CH_2$)$_n$PhNH$_2$, or of saccharide-O($CH_2$)$_n$NH$_2$ to coupled peptide and where n is an integer from 0 to 7 or higher.

17. The material according to claim 1 where the protein is albumin, and the polysaccharide is dextran.

18. The material according to claim 1 where the saccharide is at least one of the Blood group A-determinant, Blood group B-determinant, one or several of Galα1–3Galα-, Galα1–3Galβ-, Galα1–3Galβ1–4Glcβ-, Galα1–3Galβ1–4GlcNAcβ-, Galα1–3Galβ1–4GlcNAcβ1–3Galβ1–4Glcβ-, or of oligomeric ligands, such as (Galα1–3Galα-)n-, (Galα1–3Galβ-)n-, (Galα1–3Galβ1–4Glcβ-)n-, (Galα1–3Galβ1–4GlcNAcβ-)n-, (Galα1–3Galβ1–4GlcNAcβ1–3Galβ1–4Glcβ-)n-, or (Galα1–3Galα-spacer)n-, (Galα1–3Galβ-spacer)n-, (Galα1–3Galα1–4Glcβ-spacer)n-, (Galα1–3Galβ1–4GlcNAcβ-spacer)n-, or (Galα1–3Galβ1–4GlcNAcβ1–3Galβ1–4Glcβ-spacer)n-, where n is an integer larger than 1.

19. The material according claim 1 where the saccharide is active towards antibodies against cancer-antigens, for example prostate-, breast-, intestine-, or skin cancer, or towards toxins, bacteria or virus.

20. A material according to claim 18 consisting of Blood group A—O($CH_2$)$_n$PhNH—CO—($CH_2$)$_m$NH—$CH_2$—CH(OH)—$CH_2$—O-matrix where n is an integer of 0, 1, 2, 3 or 4, and m is an integer 1, 2, 3, 4, 5, 6 or 7, and where the linkage between —O— and matrix is formed between —O— and a carbon atom in the matrix.

21. The material according to claim 18 consisting of Blood group B—O($CH_2$)$_n$PhNH—CO—($CH_2$)$_m$NH—$CH_2$—CH(OH)—$CH_2$—O-matrix where n is an integer of 0, 1, 2, 3 or 4, and m is an integer 1, 2, 3, 4, 5, 6 or 7, and where the linkage between —O— and matrix is formed between —O— and a carbon atom in the matrix.

22. The material according to claim 1 which is GalNAcα1–3(Fucα1–2)Galβ-O($CH_2$)$_2$PhNH—CO—($CH_2$)$_5$NH—$CH_2$—CH(OH)—$CH_2$—O-Matrix.

23. The material according to claim 1 containing a higher oligosaccharide than the A-trisaccharide and which contains the A-blood group determinant terminally, for example A-blood group determinant of type 1, 2, 3 or 4.

24. The material as according to claim 1 which is Galα1–3(Fucα1–2)Galβ-O(CH$_2$)$_2$PhNH—CO—(CH$_2$)$_5$NH—CH$_2$—CH(OH)—CH$_2$—O-Matrix.

25. The material according to claim 1 containing a higher oligosaccharide than the B-trisaccharide and which contains the B-blood group determinant terminally, for example B-blood group determinant of type 1, 2, 3 or 4.

26. The material according to claim 1 where the matrix is a cross-linked agarose, a filter used for plasma separation, or other matrix with corresponding properties.

27. The material according to claim 1 produced by reaction between saccharide-spacer and NHS-activated cross-linked agarose, where NHS is an abbreviation of N-hydroxysuccinimide.

28. The material according to claim 1 produced by reaction between GalNacα1–3(Fucα1–2)Galβ-O(CH$_2$)$_2$PhNH$_2$ and NHS-activated cross-linked agarose, and/or between Galα1–3(Fucα1–2)Galβ-O(CH$_2$)$_2$PhNH$_2$ and NHS-activated cross-linked agarose, where NHS is an abbreviation of N-hydroxysuccinimide.

29. The material according to claim 1 produced by reaction between saccharide-spacer and epoxy-activated matrix.

30. The material according to claim 1 produced by reaction between saccharide-spacer and epoxy activated cross-linked agarose.

31. The material according to claim 1 produced by reaction between epoxy activated cross-linked agarose and Blood group A—O(CH$_2$)$_n$PhNH—CO—(CH$_2$)$_m$NH$_2$, or Blood group B—O(CH$_2$)$_n$PhNH—CO—(CH$_2$)$_m$NH$_2$, where n or m are specified above as are Blood group A and Blood group B, respectively.

32. The material according to claim 1 where a combination of Saccharides are covalently bound the matrix.

33. The material according to claim 1 consisting of a combination of Blood group A—O(CH$_2$)$_n$PhNH—CO—(CH$_2$)$_m$NH—, and Blood group B—O(CH$_2$)$_n$PhNH—CO—(CH$_2$)$_m$NH—, where both type of compounds are bound to matrix.

34. The material according to claim 1 where bound amount of ligand is 0.01, 0.1, 1, 2, 3, 4, 5, 6, 7, 8, 9, 10, 11, 12, 13, 14, 15, 16, 17, 18, 19, 20 mmole per liter of matrix, or an amount of mmole which is between two of the above given values per liter of matrix.

35. The material according to claim 1 where the saccharide is bound, directly or indirectly, to an oligomeric substance acting as spacer or part of a spacer.

36. The material according to claim 1 where the oligomeric substance is a mono-, di-, or higher oligosaccharide or polysaccharide, or a peptide, or a protein.

37. The material according to claim 1 which in addition contains a Tris structure according to:

(HOCH$_2$)$_3$C—NH—CO—(CH$_2$)$_5$NH—CH$_2$—CH(OH)—CH$_2$—O-Matrix where (HOCH$_2$)$_3$C—NH— is a Tris-group.

38. The material according to claim 37 made by reaction between Tris-HCl and NHS-activated cross-linked agarose wherein the matrix above is sepharose 4 FF.

39. The material according to claim 38 that has been autoclaved.

* * * * *

UNITED STATES PATENT AND TRADEMARK OFFICE
CERTIFICATE OF CORRECTION

PATENT NO.        : 6,686,457 B1
APPLICATION NO.   : 09/722241
DATED             : February 3, 2004
INVENTOR(S)       : Kurt Nilsson Page 1 of 1

It is certified that error appears in the above-identified patent and that said Letters Patent is hereby corrected as shown below:

Title page, add -- Related U.S. Application Data

(63)    Continuation-in-part of application No. 09/091,486, filed on Dec. 23, 1996, now Pat. No. 6,444,655. --

Title page, add -- (30)        Foreign Application Priority Data

Jun. 28, 2000        (SE)…………..…..0002462.0
Apr. 6, 2000         (SE)…………..…..0000430.9
Nov. 24, 2000        (SE)…………..…..0004343.0 --

Signed and Sealed this

Fifth Day of December, 2006

JON W. DUDAS
*Director of the United States Patent and Trademark Office*